(12) United States Patent
Enggaard et al.

(10) Patent No.: US 8,221,356 B2
(45) Date of Patent: Jul. 17, 2012

(54) MEDICATION DELIVERY SYSTEM WITH A DETECTOR FOR PROVIDING A SIGNAL INDICATIVE OF AN AMOUNT OF A SET AND/OR EJECTED DOSE OF DRUG

(75) Inventors: Christian Peter Enggaard, Vejby (DK); Preben Nielsen, Holbæk (DK); Bodo von Munchow, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 11/665,572

(22) PCT Filed: Oct. 20, 2005

(86) PCT No.: PCT/EP2005/011282
§ 371 (c)(1), (2), (4) Date: Feb. 4, 2008

(87) PCT Pub. No.: WO2006/045523
PCT Pub. Date: May 4, 2006

(65) Prior Publication Data
US 2008/0140018 A1    Jun. 12, 2008

Related U.S. Application Data

(60) Provisional application No. 60/626,550, filed on Nov. 10, 2004.

(30) Foreign Application Priority Data

Oct. 21, 2004 (EP) .................................. 04077897

(51) Int. Cl.
*A61M 1/00* (2006.01)
*A61M 5/00* (2006.01)
*A61B 18/18* (2006.01)

(52) U.S. Cl. ........................... 604/152; 604/207; 606/41
(58) Field of Classification Search .................. 604/152, 604/207; 606/41
See application file for complete search history.

(56) References Cited

U.S. PATENT DOCUMENTS 4,515,584 A    5/1985    Abe et al.
(Continued)

FOREIGN PATENT DOCUMENTS

DE    29904864    8/2000
(Continued)

OTHER PUBLICATIONS

International Search Report for PCT/EP2005/011282 filed Oct. 20, 2005.
(Continued)

*Primary Examiner* — Nicholas Lucchesi
*Assistant Examiner* — Ian Holloway
(74) *Attorney, Agent, or Firm* — Marc A. Began

(57) ABSTRACT

A medication delivery system, comprising: a movable part (230, 232) adapted to move relative to a stationary part; at least two conductors (234, 236) which are arranged such that an electrical characteristic is defined by the mutual position of the movable and the stationary part and/or by movement of one of said parts relative to the other; and a detector for detecting a change of said electrical characteristic, wherein the parts are stationary relative to each other during dose setting and in that the parts are moved relative to each other during dose ejection, such that that detector provides a signal indicative of the actual amount of the ejected dose.

2 Claims, 12 Drawing Sheets

U.S. PATENT DOCUMENTS

| | | | |
|---|---|---|---|
| 4,592,745 A | 6/1986 | Rex et al. |
| 4,634,431 A | 1/1987 | Whitney et al. |
| 4,636,201 A | 1/1987 | Ambrose et al. |
| 4,812,724 A | 3/1989 | Langer et al. |
| 4,838,860 A | 6/1989 | Groshong et al. |
| 4,883,472 A | 11/1989 | Michel |
| 4,898,578 A | 2/1990 | Rubalcaba |
| 4,959,056 A | 9/1990 | Dombrowski et al. |
| 4,973,318 A | 11/1990 | Holm et al. |
| 4,985,015 A | 1/1991 | Obermann et al. |
| 5,002,536 A | 3/1991 | Thompson et al. |
| 5,009,640 A | 4/1991 | Pyret et al. |
| 5,017,190 A | 5/1991 | Simon et al. |
| 5,098,400 A | 3/1992 | Crouse et al. |
| 5,221,268 A | 6/1993 | Barton et al. |
| 5,272,917 A * | 12/1993 | Pippert | 73/168 |
| 5,279,586 A | 1/1994 | Balkwill |
| 5,363,842 A | 11/1994 | Mishelevich et al. |
| 5,494,036 A | 2/1996 | Uber et al. |
| 5,509,905 A | 4/1996 | Michel |
| 5,522,799 A | 6/1996 | Furukawa |
| 5,536,249 A | 7/1996 | Castellano et al. |
| 5,573,506 A | 11/1996 | Vasko |
| 5,582,598 A | 12/1996 | Chanoch |
| 5,593,390 A | 1/1997 | Castellano et al. |
| 5,662,612 A * | 9/1997 | Niehoff | 604/155 |
| 5,690,618 A | 11/1997 | Smith et al. |
| 5,704,922 A | 1/1998 | Brown |
| 5,725,508 A | 3/1998 | Chanoch et al. |
| 5,728,074 A | 3/1998 | Castellano et al. |
| 5,782,814 A | 7/1998 | Brown et al. |
| 5,795,333 A | 8/1998 | Reilly et al. |
| 5,807,336 A | 9/1998 | Russo et al. |
| 5,843,047 A | 12/1998 | Pyrozyk et al. |
| 5,873,856 A | 2/1999 | Hjertman et al. |
| 5,920,198 A * | 7/1999 | Suzuki et al. | 324/662 |
| 5,928,197 A * | 7/1999 | Niehoff | 604/155 |
| 5,947,934 A | 9/1999 | Hansen et al. |
| 5,998,989 A | 12/1999 | Lohberg |
| 6,019,745 A | 2/2000 | Gray |
| 6,235,004 B1 | 5/2001 | Steenfeldt-Jensen et al. |
| 6,268,722 B1 | 7/2001 | Kogure et al. |
| 6,482,185 B1 | 11/2002 | Hartmann |
| 6,547,755 B1 | 4/2003 | Himbert et al. |
| 7,138,806 B2 * | 11/2006 | Gafner et al. | 324/660 |
| 7,144,384 B2 * | 12/2006 | Gorman et al. | 604/131 |
| 7,195,616 B2 * | 3/2007 | Diller et al. | 604/224 |
| 2002/0029018 A1 | 3/2002 | Jeffrey |
| 2003/0055685 A1 | 3/2003 | Cobb et al. |
| 2004/0074652 A1 | 4/2004 | Ginell |
| 2004/0171983 A1 | 9/2004 | Sparks et al. |
| 2004/0207385 A1 | 10/2004 | Gafner et al. |
| 2004/0210199 A1 | 10/2004 | Atterbury et al. |
| 2005/0020969 A1 | 1/2005 | Slate et al. |
| 2005/0041531 A1 | 2/2005 | Sekura |
| 2005/0182360 A1 * | 8/2005 | Yeandel et al. | 604/96.01 |
| 2006/0047538 A1 | 3/2006 | Condurso et al. |
| 2006/0135907 A1 | 6/2006 | Remde et al. |
| 2008/0140018 A1 | 6/2008 | Enggaard et al. |
| 2008/0188813 A1 | 8/2008 | Miller et al. |
| 2009/0069742 A1 | 3/2009 | Larsen |

FOREIGN PATENT DOCUMENTS

| | | |
|---|---|---|
| DE | 10116361 | 10/2002 |
| DE | 10201875 | 5/2003 |
| DK | PA 2001 00240 | 11/2001 |
| EP | 387854 | 9/1990 |
| EP | 635277 | 1/1995 |
| EP | 1074273 | 2/2001 |
| EP | 1095668 | 5/2001 |
| EP | 1361908 | 11/2003 |
| EP | 1393764 | 3/2004 |
| EP | 04077898.7 | 10/2004 |
| EP | 1726322 | 11/2006 |
| EP | 1804868 | 12/2009 |
| FR | 2740345 | 4/1997 |
| JP | H10-89910 | 4/1998 |
| JP | 10504729 | 5/1998 |
| JP | 2003-310758 | 11/2003 |
| RU | 2080882 | 6/1997 |
| SU | 1760462 | 9/1992 |
| WO | 90/09202 | 8/1990 |
| WO | 90/10470 | 9/1990 |
| WO | WO 95/24233 | 9/1995 |
| WO | WO 97/30742 | 8/1997 |
| WO | WO 97/33638 | 9/1997 |
| WO | WO 99/15214 | 4/1999 |
| WO | WO 01/26710 | 4/2001 |
| WO | WO 02/43573 | 6/2002 |
| WO | 02/064196 | 8/2002 |
| WO | 02/092153 | 11/2002 |
| WO | 03/009461 | 1/2003 |
| WO | WO 03/005891 | 1/2003 |
| WO | WO 03/047426 | 6/2003 |
| WO | 03/103753 | 12/2003 |
| WO | 2004/030717 | 4/2004 |
| WO | 2004/030717 A2 | 4/2004 |
| WO | WO 2004/098390 | 11/2004 |
| WO | WO 2004/098390 | 12/2004 |
| WO | WO 2005/042076 | 5/2005 |
| WO | WO 2006/045525 | 5/2006 |
| WO | 2006087712 A2 | 8/2006 |

OTHER PUBLICATIONS

Tränkler, 1996, "Taschenbuch Der Messtechnik," R. Oldenbourg Verlag München Wien pp. 181, 190.

International Search Report from PCT/EP2007/052636, mailed Jul. 30, 2007.

DE 29904864 English Abstract, published Aug. 3, 2000.

DE 10201875 English Abstract, published May 22, 2003.

DE 10116361 English Abstract, published Oct. 10, 2002.

FR 2740345 English Abstract, published Oct. 26, 1995.

Final Office Action mailed Aug. 9, 2010 in U.S. Appl. No. 11/665,623, filed Feb. 4, 2008 by Miller et al.

Non-Final Office Action mailed Mar. 29, 2010 in U.S. Appl. No. 11/665,623, filed Feb. 4, 2008 by Miller et al.

Final Office Action mailed Apr. 10, 2009 in U.S. Appl. No. 11/665,623, filed Feb. 4, 2008 by Miller et al.

Non-Final Office Action mailed Oct. 27, 2008 in U.S. Appl. No. 11/665,623, filed Feb. 4, 2008 by Miller et al.

Notice of Allowance mailed Aug. 31, 2005 in U.S. Appl. No. 10/076,025, filed Feb. 13, 2002 by Larsen et al.

Non-Final Office Action mailed Nov. 28, 2003 in U.S. Appl. No. 10/076,025, filed Feb. 13, 2002 by Larsen et al.

* cited by examiner

MEDICATION DELIVERY SYSTEM WITH A DETECTOR FOR PROVIDING A SIGNAL INDICATIVE OF AN AMOUNT OF A SET AND/OR EJECTED DOSE OF DRUG

CROSS-REFERENCE TO RELATED APPLICATIONS

This application is a 35 U.S.C. §371 national stage application of International Patent Application PCT/EP2005/011282(published as WO 2006/045523), filed Oct. 20, 2005, which claimed priority of European Patent Application 04077897.9, filed Oct. 21, 2004; this application further claims priority under 35 U.S.C. §119 of U.S. Provisional Application 60/626,550, filed Nov. 10, 2004.

FIELD OF THE INVENTION

The present invention relates to a medication delivery system comprising a detector for detecting relative rotational movement and/or position of a movable part and a stationary part.

BACKGROUND OF THE INVENTION

In medication management, compliance i.e. the degree to which a patient follows medical instructions and protocols, is often of extreme importance. In relation to injection of medicaments, one key aspect of determining the compliance is determination of the actual dose of the medication injected. Accordingly, it is desirable to provide medication delivery systems with dose quantity identification systems.

One such system is known from WO 02/092153, which discloses a medication injector apparatus, which encompasses a doseable quantity identifier for an injector pen vvhich uses a sensor to read a matrix to determine how a dose setting mechanism has been rotationally arranged by a user in setting the pen for dose administration. The apparatus further comprises an assembly for selectively rotating a drive sleeve, which assembly has a dial that rotates out during dose setting and which translates without rotation during dose injecting.

Further dose quantity identification systems may be seen in WO 03/103753, WO 2004/030717, WO 90/09202, WO 03/009461 and WO 02/064196.

It is an object of a preferred embodiment of the present invention to provide a medication delivery system, which rather than outputting the dose which is assumed to be ejected, outputs the dose which in fact was ejected.

BRIEF SUMMARY OF THE INVENTION

The present invention provides a medication delivery system, comprising:
 a movable part adapted to move relative to a stationary part;
 at least two conductors which are arranged such that an electrical characteristic is defined by the mutual position of the movable and the stationary part and/or by movement of one of said parts relative to the other; and
 a detector for detecting a change of said electrical characteristic,
wherein
the parts are stationary relative to each other during dose setting and in that the parts are moved relative to each other during dose ejection, such that that detector provides a signal indicative of the actual amount of the ejected dose.

One advantage of the present invention is that the system identifies the actual amount of the ejected dose, as it does not assume that the ejected dose is identical to the set dose. Thus, any difference between the set dose and the ejected dose will not influence the determination of compliance. Such difference between the set dose and the ejected dose could e.g. occur if the ejection process be halted during dose ejection.

The medication delivery system may be a syringe device comprising an integrated reservoir for accommodation of a medicament. In other embodiments the reservoir is removable and thus a new reservoir may be inserted into the device when a used reservoir is empty. The system may form a pen e.g. for insulin.

The movable part may be movable by translation or by rotation. The stationary part may co-axially encapsulate the movable part e.g. such that both co-extend in an axial direction of the device and such that the movable part is provided inside the stationary part. A housing of the syringe device may define the stationary part. In other embodiments the stationary part is attached to the housing of the device.

The movable part may be connected to a piston rod of the device, the piston rod being employed for advancing a piston for forcing drug out of a drug-containing compartment of the system. Translational movement of the piston rod may cause a part of the medicament of be ejected from the syringe device. The piston rod may have a threaded outer surface and a part of the device may be adapted to receive the piston rod as it has a corresponding threaded inner surface. In the latter embodiment rotational movement of the piston rod may also result in a translational movement of the piston rod.

In one embodiment the movable part and the stationary part is able to rotate more then one revolution i.e. more than 360 degrees, during setting of the dose or during ejection. In such embodiments the medical device may comprise a counter which is able to count the number of revolutions performed.

In the device there is provided at least two conductors between which the detector may be provided. Alternatively, the detector may be connected to the electrical conductors of the device. As an example a resistance between the conductors changes depending on the relative position of the movable part and the stationary part and thus the detector may be a device adapted to detect resistance between two elements.

In embodiments wherein the movable part is adapted to rotate relative to the stationary part during ejection of a set dose of a medicament, the detector may be used to determine the ejected dose such that the user may keep a log of the ejection history and the ejection times.

In embodiments wherein the movable part is adapted to rotate relative to the stationary part during setting of a dose, there may be provided a sensor which is able to determine when an ejection starts and/or when it is finished. Thus, the ejected dose may be calculated using information about the set dose at the time of starting the ejection and the remaining dose when finishing the ejection. In the latter embodiment detector may be a detector capable of determining translational movement e.g. of the piston rod, but not necessarily the length of the traveled distance.

In case the movable part is movable by translation, such as linear translation, the movable part may e.g. constitute a portion of the piston rod, or it may constitute a part which is integral with the piston rod.

The electrical characteristic may be one of an electrical inductance, a capacitance, an electric resistance, a voltage and an electrical current. The electrical inductance may e.g. be impedance or capacitance. In the latter case the electrical conductors may be connected to surfaces of conductive material which are spaced apart from each other. The relative position of the two surfaces determines the capacitance. In one embodiment the surfaces are provided as two half circles which may be rotated between two positions a first position wherein they overlap each other entirely and a second position wherein the do not overlap at all. In an alternative to the latter embodiment one of the surfaces moves translationally while rotating, whereby the distance between the surfaces changes. Thus, when the movable part has rotated one revolution the capacity between the plates has changed as the distance between the plates has changes. Thus, it is possible to determine both the relative angular position of the surfaces and the number of revolutions which have been performed.

In yet another embodiment a coil may be provided between the two conductors. The coil may be provided on stationary part. At the same time a magnetic material may be provided on the movable part and thus movement of the movable part induces a current between the two conductors. In the latter embodiment the relative movement of the stationary part and the movable part may be determined.

From the above it may be appreciated that the electrical characteristic between the two conductors may depend on relative position and or on relative movement of the movable part and the stationary part.

The movable part may comprise a first electrically conducting surface, and the stationary part may comprise a second electrically conducting surface, the electrical characteristic of the at least two electrical conductors being determined by relative movement and/or relative position of said first and second surfaces. In one embodiment there is provided two conductors a first which is electrically connected to the first electrically conducting surface and a second conductor which is electrically connected to the second electrically conducting surface.

A primary set of contact surfaces may be arranged to engage and disengage upon relative movement of the stationary part and the movable part, the primary set of contact surfaces may comprise a first and a second contact surface which comprises the first and the second electrical surfaces, respectively.

In a preferred embodiment the first conductor is connected to the first conducting surface which is provided on the first contact surface and the second conductor is connected to the second conducting surface which is provided on the second contact surface.

In one embodiment a secondary set of contact surfaces may be arranged to engage and disengage upon relative movement of the stationary part and the movable part, the secondary set of contact surfaces may comprise a third and a fourth contact surface which may comprise a third and a fourth electrical surface, respectively. Furthermore, the electrical characteristic between the primary set of contact surfaces may be unchanged when the electrical characteristic between the secondary set of contact surfaces is changed and vice versa. Thus, at no time two or more electrical characteristic are changed at the same time.

In one embodiment the rotatable part comprises both the first and the third electrically conducting surfaces which are provided on the same contact surfaces.

Biasing arms may be provided which are biased towards the periphery of the movable part, said arms comprising at least one of the second and the fourth conducting surfaces. In one embodiment there is provided two biasing arms one defining the second conducting surface and one defining the fourth conducting surface.

The outer periphery of the movable part may define a plurality of conductive and non-conductive surfaces which may define the first and the third contact surfaces.

A visible and/or audible and/or tactile indication may detectable when the second or the fourth contact surface changes from a conductive to a non-conductive surface. Accordingly, the system changes status electronically, the user may be able to identify a change e.g. as he hears or feels a 'click'.

The periphery of the movable part, may comprise abrupt changes in the radial dimension. Such abrupt changes may be used to ensure that the movable part is only able of rotating in one direction. The changes may also be used to provide a tactile or audible indication which may be generated by rotating the movable part such that an biased arm changes position from a point with a large radial dimension to a point with a small radial dimension, where by a 'click' may be generated.

The contact surfaces may arranged to lock for relative rotational movement in one direction. The lock may be provided by the abrupt change in the radial dimension.

A processor may be provided to collect the information detected from the detector. Such a processor may be an electronic processor comprising a memory. In one embodiment the arrangement comprises a power supply and an ASIC connected to the at least two conductors. The ASIC may be adapted to collect the information from the detector and to transform the information into a format known to the user. As an example the collected information is in one embodiment degrees of rotation of the movable part relative to the stationary part. In the embodiment rotation of a piston rod results in rotation of the movable part and as the outer surface of the piston rod is threaded, rotation of the piston rod results in a translational movement of the piston rod such that volume of the medicament is ejected. Accordingly, the ASIC of said embodiment may transform the degrees of rotation into a distance in the axial direction which again may be transformed into the volume of the medicament which is ejected.

DETAILED DESCRIPTION OF THE INVENTION

The invention will now be described in further detail with reference to the drawings, in which.

Figure 1:
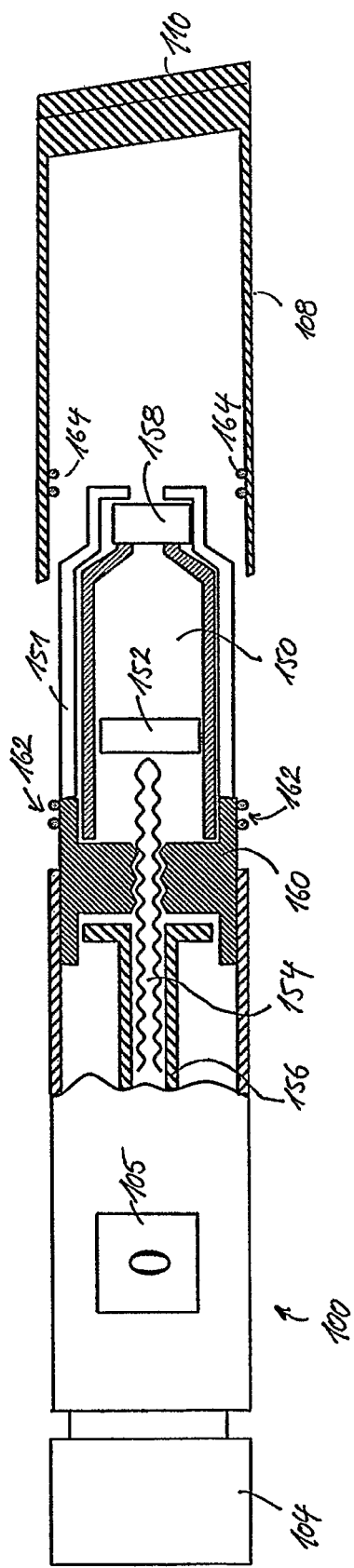
FIG. 1 is a schematic cross-sectional illustration of a medication delivery pen and a cover therefor.

The pen 100 in FIG. 1 includes a drug cartridge or container 150, in which a piston 152 is arranged, so that it may slide in a distal direction (to the right in FIG. 1) under the action of a piston rod 154. The cartridge is secured in relation to the remaining parts of the pen by a cartridge holder 151. The piston rod 154 has a threaded outer surface which is guided in a ratchet 156. When drug ejection is activated by an operator, the ratchet and/or piston rod is influenced to cause the piston rod to move the piston 152 in the distal direction to force the drug out of the cartridge 150 through a needle (not shown) which extends through septum 158. Evidently, the cover 108 is removed prior to ejection of the dose. The pen further includes a nut 160 with an integrated sensor arrangement for detecting the size of an ejected dose, the sensor arrangement being further described below in connection with FIGS. 3-12. Electrical switches 162 provide an interface to external devices, such as to a cradle for transmitting information to an external device, such as a personal computer, or to a pen cover 108 which includes corresponding switches 164. The cover 108 may include a battery (not shown) for powering its display portion 110. The battery may conveniently be comprised in the distal end portion of the cover. A rotational dose setting member 104 may be used to set a dose, the set dose being e.g. indicated in a window 105. In general, the rotational movement of the piston rod 154 during ejection of the drug may be achieved as described in U.S. Pat. No. 6,235,004 which is hereby incorporated by reference.

Figure 2:
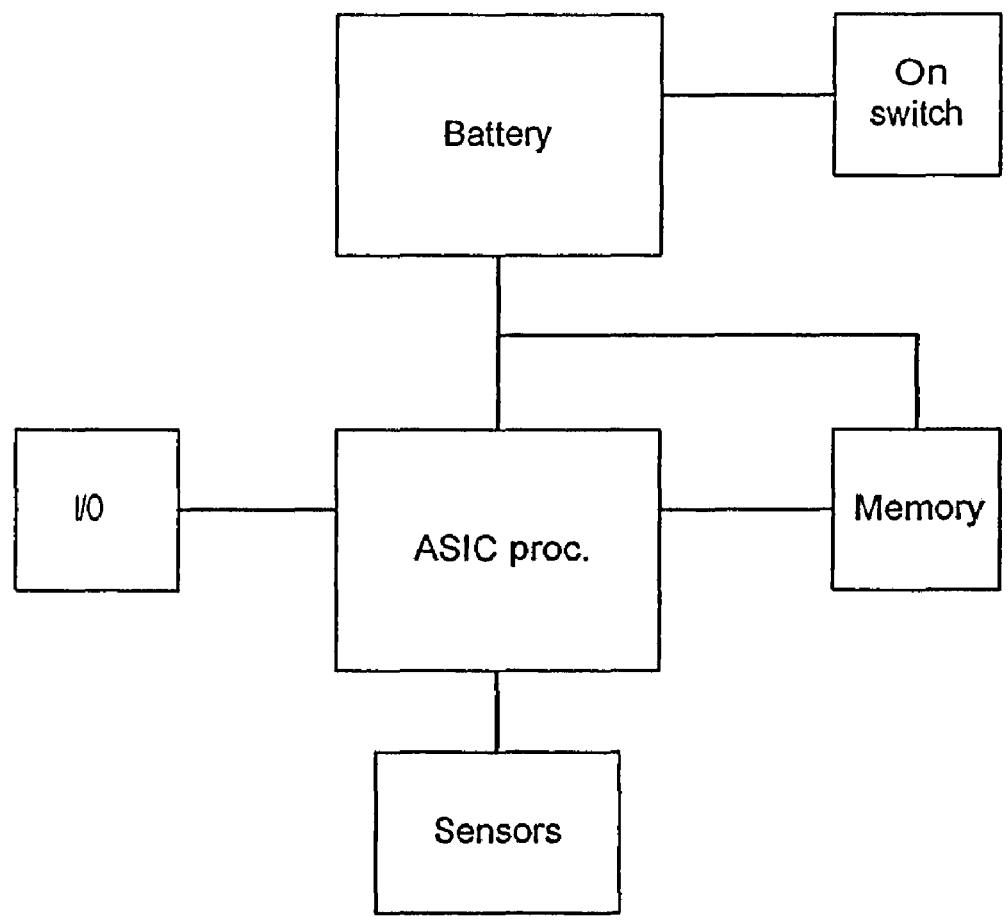
FIG. 2 is a schematic illustration of electronic components of an embodiment of a medication delivery pen.
Figure 3:
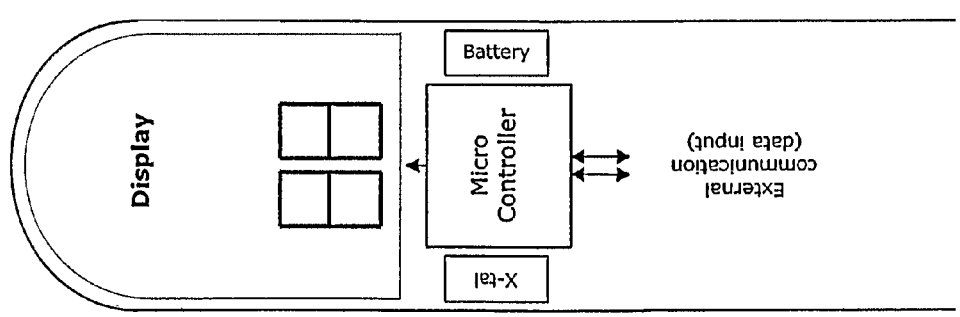
FIG. 3 is a schematic illustration of electronic components of an embodiment of a cover for a medication delivery pen.

FIG. 2 is a schematic illustration of electronic components of an embodiment of a medication delivery pen. There is provided an "On switch" for allowing the battery to deliver power to an ASIC processor and to a memory connected to the ASIC processor. The processor is further connected an I/O device for communicating data via the switches 162 (cf. FIG. 1), and to one or more sensors, e.g. a sensor arrangement for detecting ejection information. In operation, the sensors may detect the quantity of an ejected dose which is communicated to the ASIC processor. The processor stores the quantity and the time of the ejection in the memory. Once the pen 100 is placed in the cradle 114 or once the cover 108 is placed over the needle portion of the pen, the ASIC processor initiates transfer of the information stored in the memory or a part of that information via the I/O device. The I/O device may also be used to clear the memory, such clearing being e.g. caused by an operator of the personal computer 112. The electronic components incorporated in the pen cover or cap 108 are illustrated in FIG. 3. A crystal (X-tal) serves as a clock generator for the microcontroller, which is powered by a battery, and which communicates with the electronic components of the pen via the external communication (data input) and with the display as illustrated.

Figure 4:
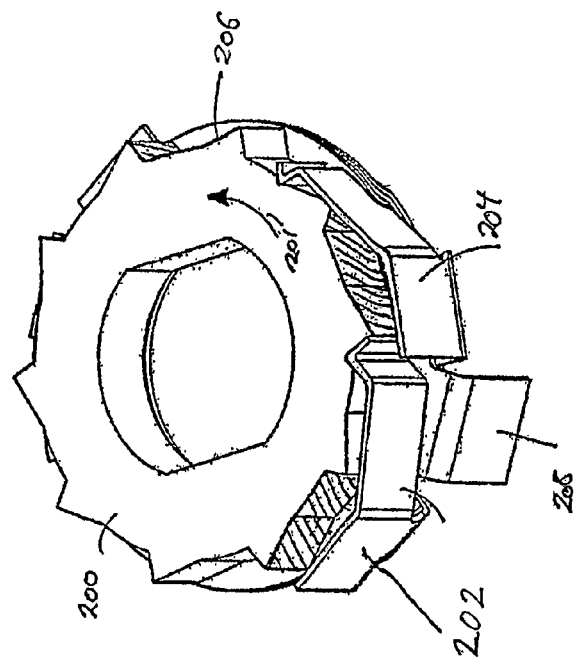
FIGS. 4-15 illustrate various parts of a sensor arrangement for detecting a quantity of a dose of drug ejected from an embodiment of medication delivery pen, the movable part of which is rotational.

The nut 160 may for example constitute a part of the sensor arrangement of FIG. 4. The sensor arrangement comprises a first conductor in the form of a movable part 200 arranged to rotate in the direction of arrow 201 in relation to one or more second conductors in the form of stationary parts, e.g. arms 202 and 204, which are biased toward a peripheral edge 206 of the movable part 200. The hatched sections of the periphery 206 are non-conductive surface portions, whereas the non-hatched sections are conductive surface portions, i.e. first and third contact surfaces. Those end portions of the arms 202 and 204 which engage the periphery 206 define second and fourth contact surfaces. It will thus be appreciated that one of the arms via its engagement with the peripheral surface portion 206 defines a primary set of contact surfaces, while the other one of the arms via its engagement with the peripheral surface portion 206 defines a secondary set of contact surfaces. A conductive element 208 is provided for applying a voltage to the movable part 200. As illustrated, the periphery 206 defines abrupt changes of its radial dimension. These abrupt changes are also abrupt changes between conductive and non-conductive surface portions. Accordingly, as the movable part 200 is rotated relative to the arms 202 and 204, each of the arms will be charged in an alternating manner in accordance with its engagement with a conductive, i.e. charged, surface portion, or with a non-conductive, i.e. non-charged, surface portion. The changes in the two arms' respective charges can be recorded or detected, so that each voltage change in either one of the arms indicates a rotational increment of the movable part. This increment may indicate an incremental increase or decrease of a set dose, and/or an incremental increase of an ejected dose. Thanks to the abrupt changes in radial dimension of the movable part 200 and corresponding abrupt changes in surface conductivity, there is provided a mechanical coupling between the changes of the electrical characteristic and the rotation of the movable part. Accordingly, it is ensured that no increment is erroneously recorded without the movable part having actually been rotated.

Figure 5:
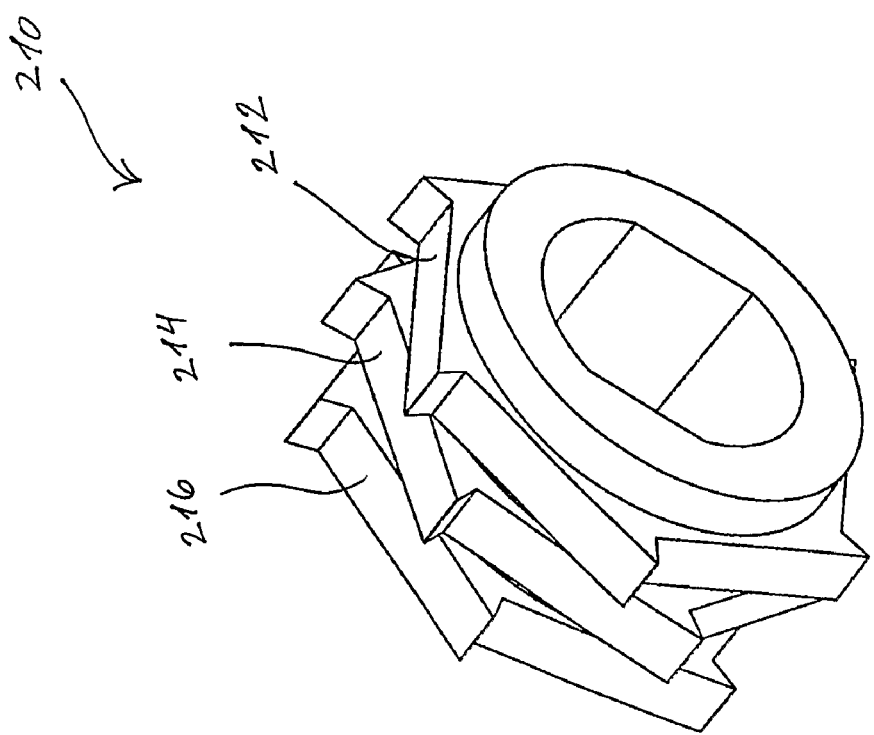

FIG. 5 illustrates a different embodiment of a movable part 210 for determining an ejected and/or set dose. The peripheral surface of the part 210 comprises three sections 212, 214 and 216, each of which defines a plurality of abrupt changes of radial dimension and conductivity according to the same general principle as described above in connection with FIG. 4. The abrupt changes of each of the three sections are arranged with mutual angular displacements in order to decrease the detectable increments of a set or ejected dose portion which.

Figure 6:
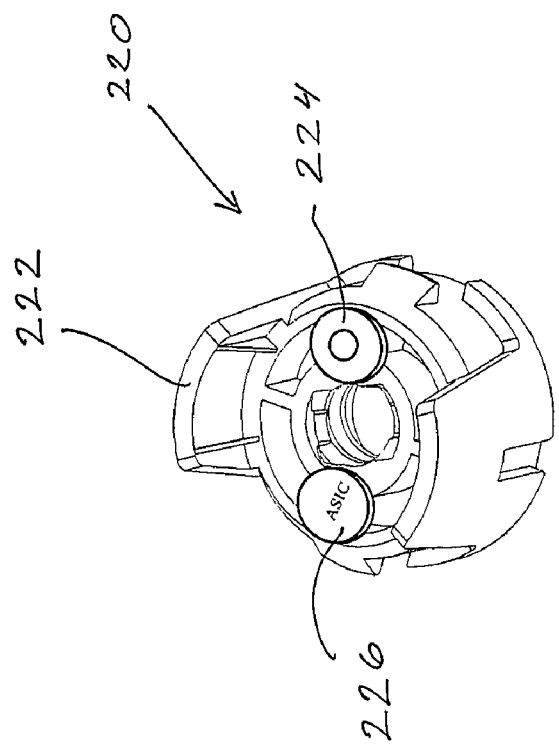

The sensor assembly 220 depicted in FIG. 6 includes the movable part 200 of FIG. 4 or the movable part 210 of FIG. 5 integrated with a support member 222 for mounting the sensor assembly in a housing of a medication delivery pen. The support member 222 also supports a battery 224 and a processor 226, such as an ASIC processor.

Figure 7:
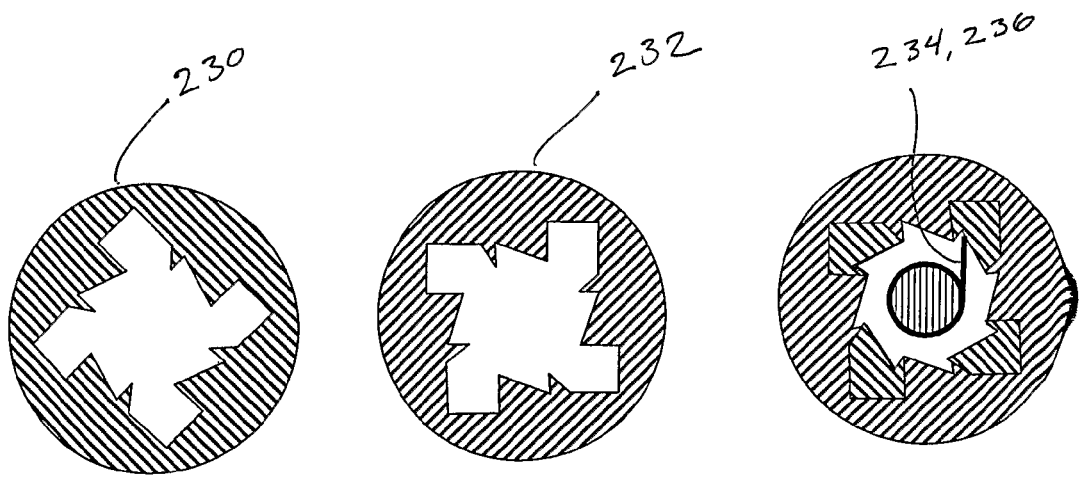
Figure 8:
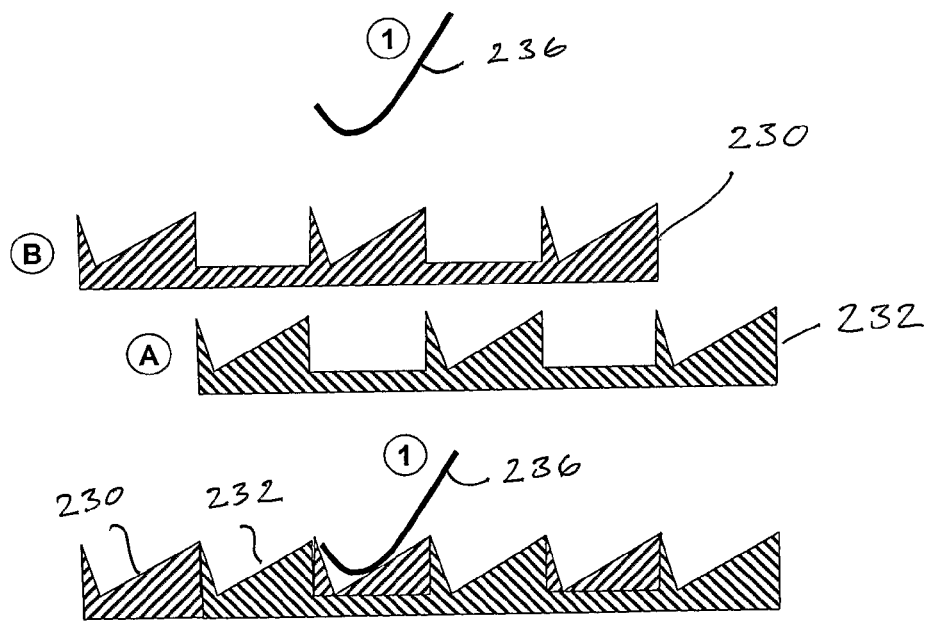
Figure 10:
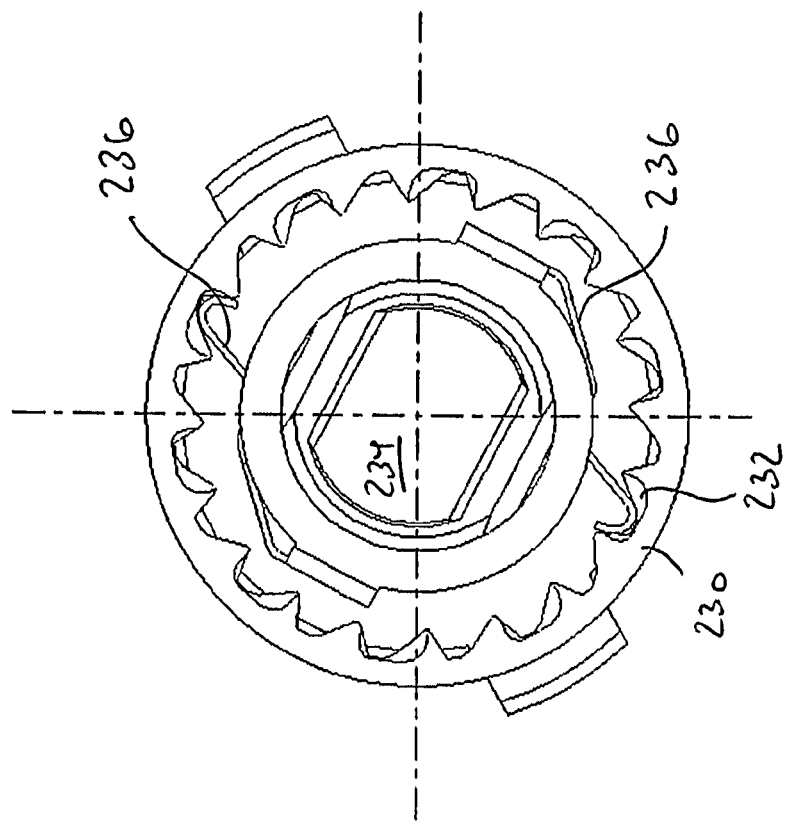
Figure 9:
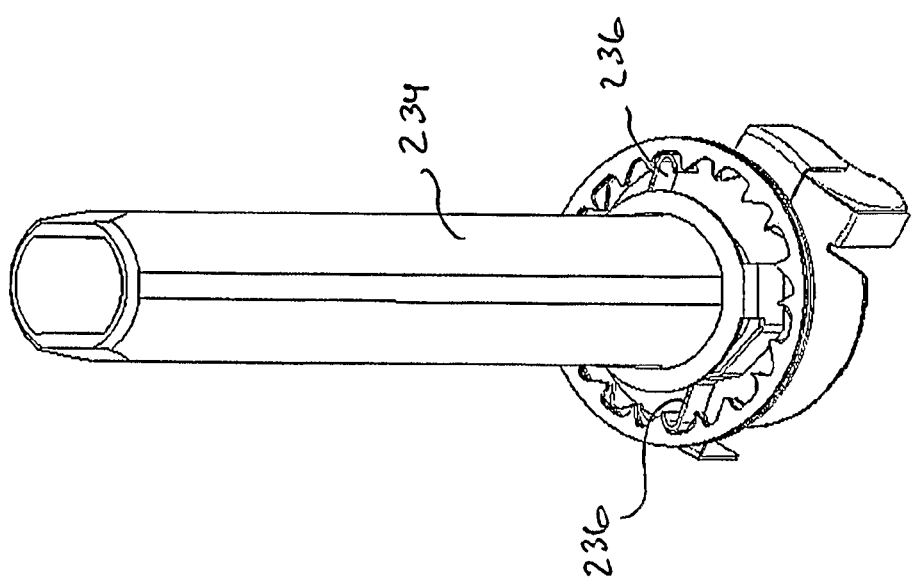

The embodiment of FIGS. 7-10 comprises two identical discs 230 and 232 arranged one above the other with a mutual angular displacement as illustrated in the far right drawing of FIG. 7. A core member 234 is arranged centrally within the discs, the core member carrying a ratchet arm 236 for engagement with one or the other disc. The discs are charged differently and arranged in electrical isolation from one another, so that the ratchet arm will produce a voltage output which varies as the ratchet arm 236 makes contact with one or the other disc 230, 232, cf. the illustrative view in the lower drawing of FIG. 8. As shown in FIGS. 9 and 10, there may be provided two arms 236. The core member may, cf. FIG. 9, extend out of the plane of the discs, so that rotation thereof may be effected by rotation of e.g. a dose setting member and/or a dose ejecting means (not shown in FIG. 9) connected to or integrated with the core member 234.

Figure 11:
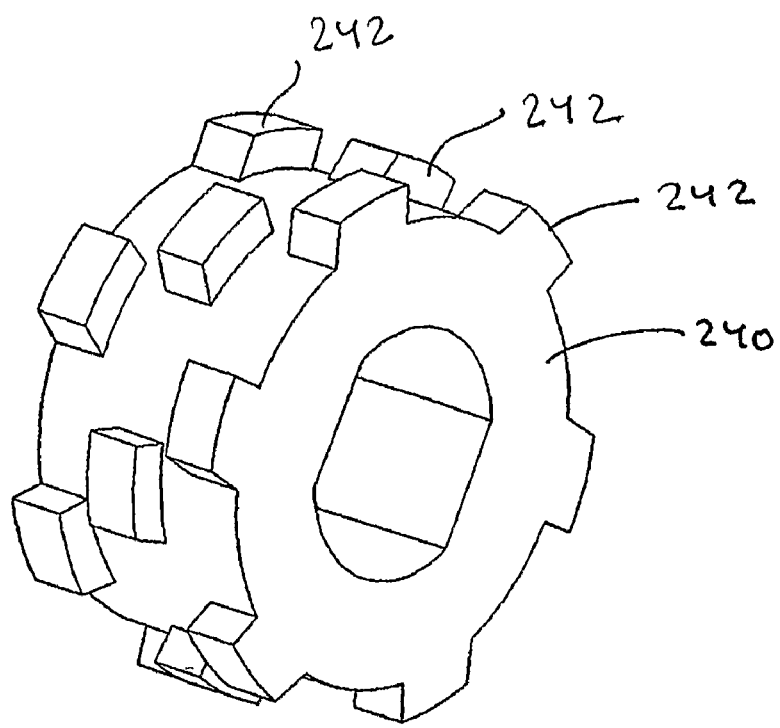
Figure 12:
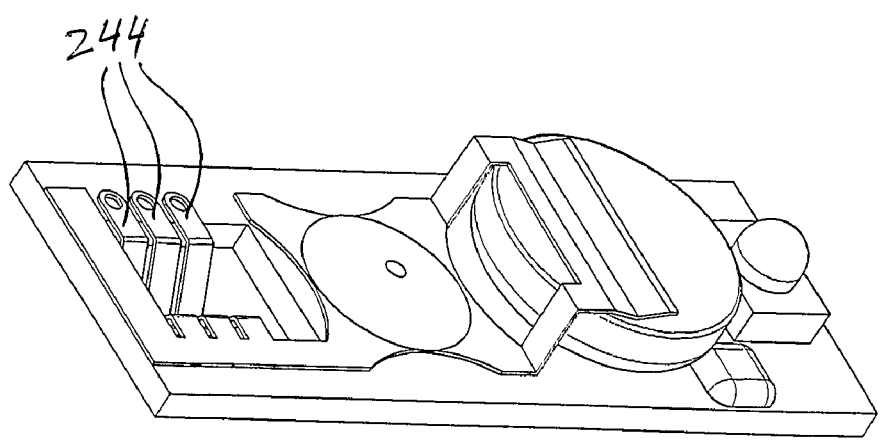

FIG. 11 shows a yet further embodiment of a movable part 240 which comprises three rows of protrusions 242 along its periphery. For example, the peripheral surfaces of the protrusions may be conductive, whereas the remaining peripheral surface of the movable part 240 may be non-conductive. The part 240 forms part of a sensor arrangement which also comprises an electronic circuit board as illustrated in FIG. 12, which comprises three arms 244 for engaging and disengaging the protrusions 242 to detect rotation of the movable part 240.

Figure 13:
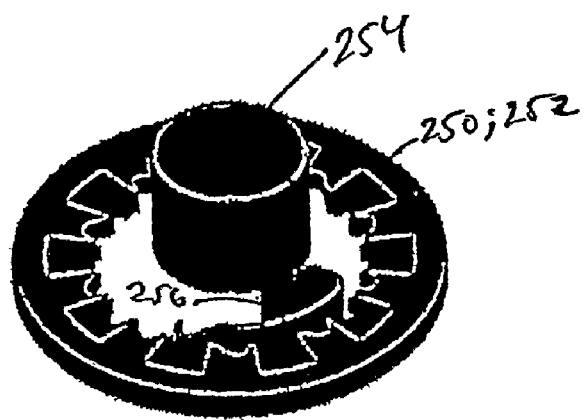

The sensor arrangement of FIG. 13 is similar to the arrangement of FIGS. 7 and 8 and comprises two discs at different voltages which are electrically insulated from one another. A core member 254 with a ratchet arm 256 makes alternating contact with one or the other disc to result in an alternating voltage output indicative of an increment or decrease of a set or an ejected dose of drug.

In the above embodiments, the electrical characteristic is described as a voltage. It should, however, be understood that the characteristic may also be any other detectable electrical property, such as a frequency of an alternating current.

Figure 14:
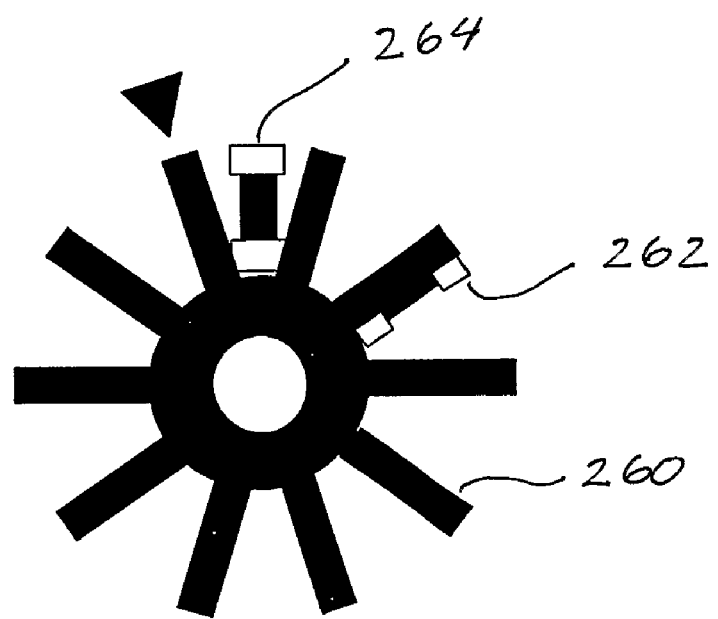

FIG. 14 illustrates an inductive sensor, in which a movable part is provided in the form of an anchor 260 to inductors 262, 264. Induction can be measured or detected by an oscillating circuit, in which frequency changes are determined, or in which the rise time of the current in the inductor can be measured.

Figure 15:
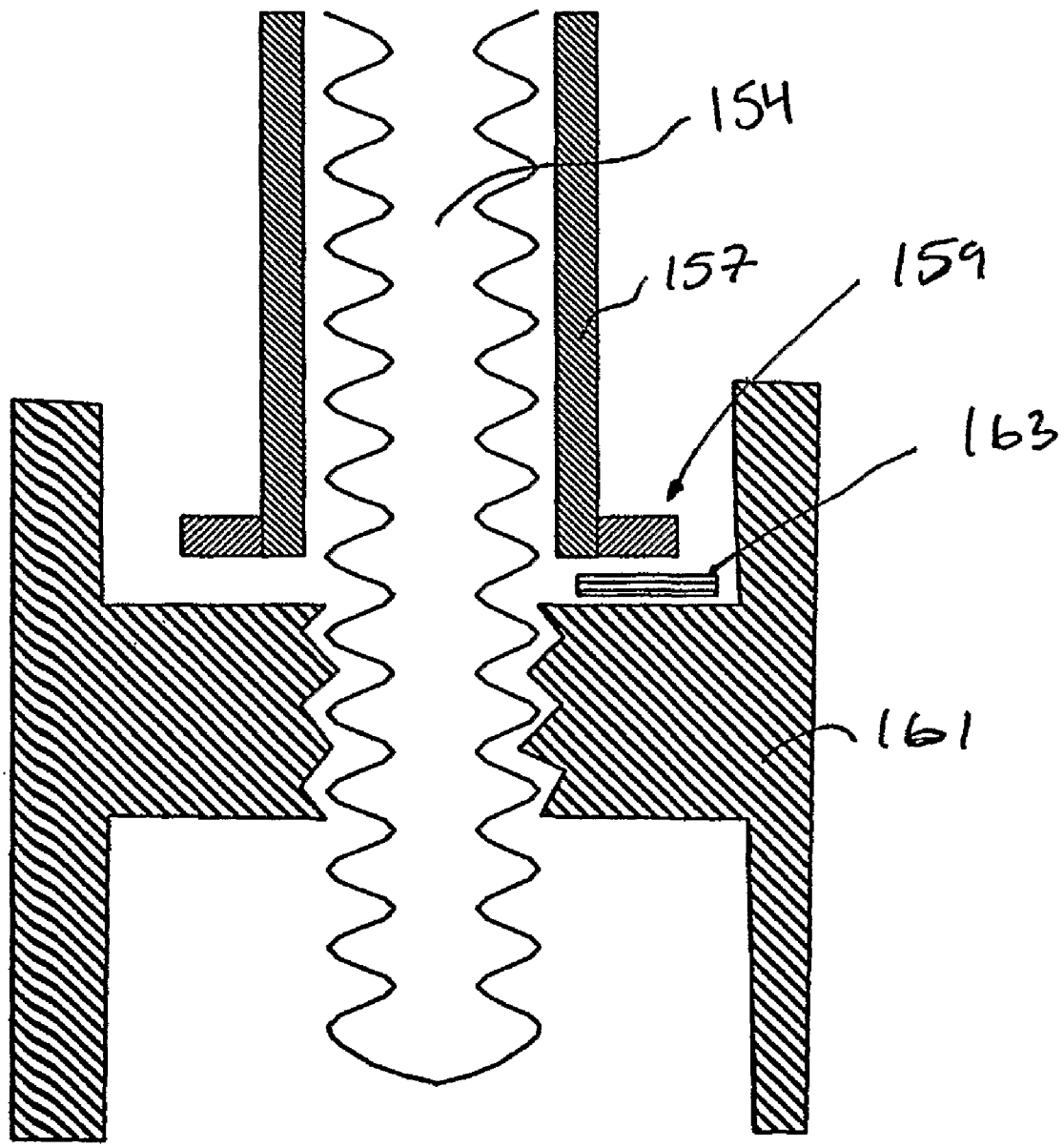

The embodiment of FIG. 15 also relies on an inductive principle, in which piston rod 154 is guided in a nut 161, the piston rod being enclosed by a conductive member 157, an end flange 159 of which is arranged in the vicinity of a coil.

Figure 16:
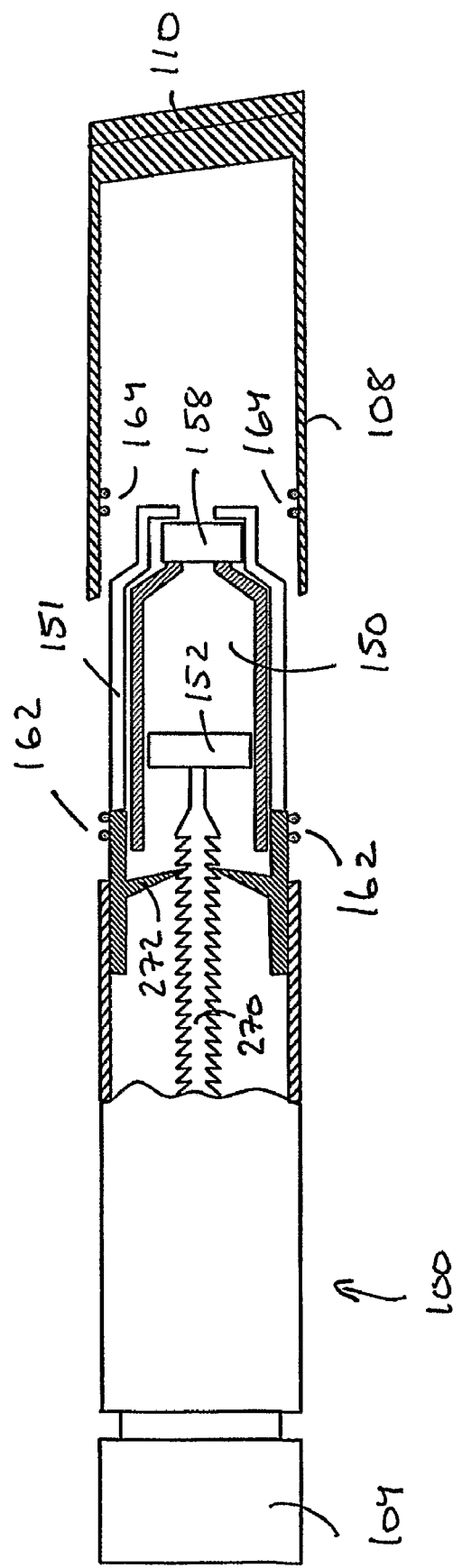
FIGS. 16-18 illustrate embodiments, the movable part of which is movable by translation.
Figure 18:
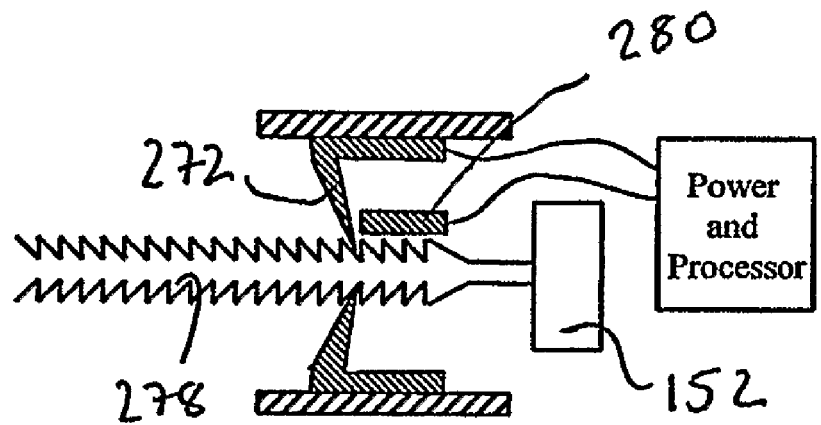
Figure 17:
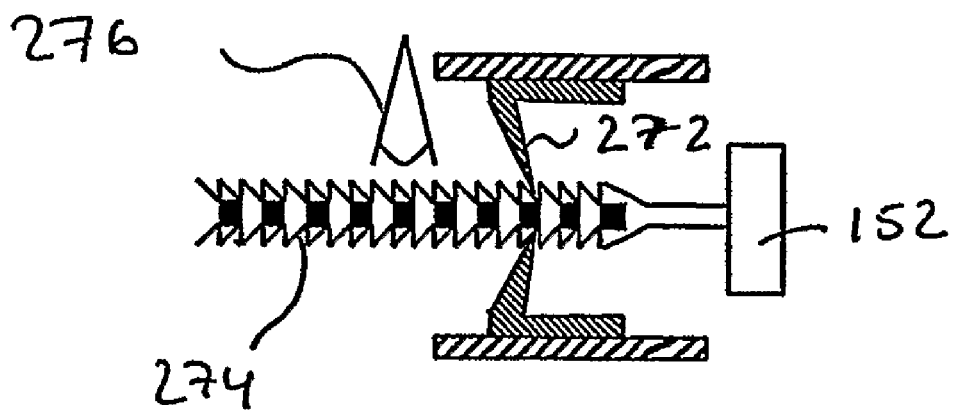

FIGS. 16-18 illustrate embodiments, the movable part of which is movable by translation.

In FIGS. 16-18, the characteristic may, as previously discussed, also be any other detectable electrical property, such as a frequency of an alternating current. To the extent that alike parts are included in the embodiment of FIGS. 16-18 as in the embodiment of FIGS. 1-15, the same reference numerals are used. Piston rod 270 has a barbed surface engaging a ratchet 272, the ratchet serving to lock the piston rod against translational movement in the proximal direction and/or as a contact for detecting advancement of the piston rod 154 in the distal or proximal direction. In FIG. 17, the piston rod 274 comprises dark and light portions which reflect and absorb light to a different extent, so that an adequate light sensor 276 may provide a signal when the piston rod is advanced in one direction or the other. The ratchet 272 serves to lock the piston rod against translational movement in the proximal direction. In FIG. 18, the engagement of the piston rod 278 and the ratchet 272 causes the ratchet to touch a contact element when the tip of the ratchet 272 passes a peak on the barbed surface of the piston rod 278. Thereby, an electrical pulse is generated each time the piston rod is advanced a distance corresponding to the distance between two successive barbs.

In general, the translational movement of the piston rod 270, 274, 278 during ejection of the drug may be achieved as described in German document DE 68901190, which is hereby incorporated by reference.

Figure 19:
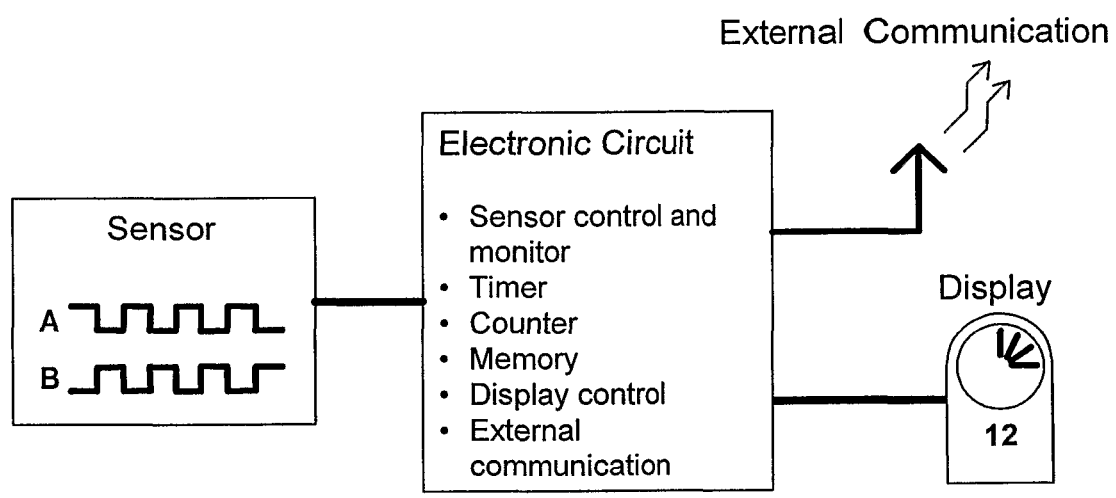
FIG. 19 illustrates a control system of the various embodiments of medication delivery pens.

The control system of any of the sensor arrangements outlined above is diagrammatically illustrated in FIG. 19, in which the sensor itself outputs signals A and B and optionally further signals depending on the number of ratchet arms or other measurement members provided. The signals are passed to an electronic circuit comprising: sensor control and monitor, timer, counter, memory, display control and external communication means. The electronic circuit is arranged to communicate with a display of a medication delivery pen and/or with an external device.

The invention claimed is:

1. A medication delivery device (100), comprising:
   A piston rod (154) for advancing a piston (152) for forcing drug out of a drug containing compartment (150) of a housing (151, 160),
   a movable part (156) connected to the piston rod (154) and adapted to rotate relative to the housing (151, 160) to move the piston rod (154) distally with sufficient force to expel the drug from the delivery device;
   at least two conductors comprising a first electrically conducting surface (200) and a second electrically conducting surface (202) which are arranged such that an electrical characteristic is defined by the mutual position of the movable part (156) and the housing (151, 160); and
   a detector for detecting a change of said electrical characteristic, wherein the movable part (156) comprising the first electrically conducting surface (200) and the housing (151, 160) comprising the second electrically conducting surface (202) are stationary relative to each other during dose setting and in that the movable part (156) and the housing (151, 160) are rotated relative to each other during dose ejection, such that the detector provides a signal indicative of the actual amount of the ejected dose.

2. A pen according to claim 1, wherein the electrical characteristic is one of an electrical inductance, a capacitance, an electric resistance, a voltage and an electrical current.

* * * * *